(12) United States Patent
Nadjafizadeh et al.

(10) Patent No.: US 6,761,168 B1
(45) Date of Patent: Jul. 13, 2004

(54) GAS SUPPLY DEVICE FOR SLEEP APNEA

(75) Inventors: Hossein Nadjafizadeh, Villers-les-Nancy (FR); Pascal Nicolazzi, Laxou (FR); Véronique Griller Lanoir, Besançon (FR)

(73) Assignee: Mallinckrodt Developpement France (FR)

( * ) Notice: Subject to any disclaimer, the term of this patent is extended or adjusted under 35 U.S.C. 154(b) by 0 days.

(21) Appl. No.: 09/913,296

(22) PCT Filed: Feb. 10, 2000

(86) PCT No.: PCT/FR00/00333
§ 371 (c)(1),
(2), (4) Date: Nov. 8, 2001

(87) PCT Pub. No.: WO00/47261
PCT Pub. Date: Aug. 17, 2000

(30) Foreign Application Priority Data

Feb. 12, 1999 (FR) .............................. 99 06516

(51) Int. Cl.$^7$ ............................................. A61M 16/00
(52) U.S. Cl. ............................ 128/204.23; 128/204.21; 128/204.18
(58) Field of Search ....................... 128/204.18, 204.21, 128/204.23

(56) References Cited

U.S. PATENT DOCUMENTS

| 5,245,995 A | 9/1993 | Sullivan et al. ......... 128/204.23 |
| 5,335,654 A | 8/1994 | Rapoport ............... 128/204.23 |
| 5,458,137 A | 10/1995 | Axe et al. .............. 128/204.23 |
| 5,490,502 A | 2/1996 | Rapoport et al. ....... 128/204.23 |
| 5,598,838 A | 2/1997 | Servidio et al. ........ 128/204.23 |
| 5,645,053 A | 7/1997 | Remmers et al. ....... 128/204.23 |
| 5,704,345 A | * 1/1998 | Berthon-Jones ........ 128/204.23 |
| 5,803,066 A | 9/1998 | Rapoport et al. ....... 128/204.23 |
| 5,823,187 A | 10/1998 | Estes et al. |
| 6,398,739 B1 | 6/2002 | Sullivan et al. .............. 600/529 |

FOREIGN PATENT DOCUMENTS

| EP | 0 651 971 A1 | 5/1995 |
| EP | 0661 071 B1 | 7/1995 |
| WO | WO 92/11054 | * 7/1992 |
| WO | WO 92/11054 A1 | 7/1992 |
| WO | WO 92/22244 A1 | 12/1992 |
| WO | WO 94/06499 A1 | 3/1994 |
| WO | WO 94/23780 | * 10/1994 |
| WO | WO 94/23780 A1 | 10/1994 |
| WO | WO 97/14462 A1 | 4/1997 |
| WO | WO 97/28838 | * 8/1997 |
| WO | WO 97/28838 A1 | 8/1997 |

* cited by examiner

Primary Examiner—Aaron J. Lewis
(74) Attorney, Agent, or Firm—Fulwider Patton Lee & Utecht LLP

(57) ABSTRACT

Methods and apparatus for controlling air supplied under pressure to a patient suffering from sleep disorders such as apnoea. Controlled pressurized air is supplied to the patient's upper anatomical airways by the apparatus according to the methods of the present invention. The apparatus measures the air flow and pressure to the airway, and determines whether to increase or decrease the pressure based on a determination of several factors, such as the occurrence of an obstructive or central apnoea, hyperventilation, air leakage and acoustical vibrations. Occurrences of apnoeas may be stored by the apparatus and read by a clinician at a later date.

18 Claims, 13 Drawing Sheets

GAS SUPPLY DEVICE FOR SLEEP APNEA

CROSS-REFERENCE TO RELATED APPLICATIONS

This application has been filed under 35 U.S.C. § 371 and claims priority to WIPO international application serial number PCT/FR00/00333, which claims priority to the French national application serial number 99/06516.

BACKGROUND OF THE INVENTION

The invention concerns a method of controlling an apparatus for supplying air pressure to a patient suffering from sleep problems.

The invention also concerns an apparatus for supplying air pressure to a patient suffering from sleep problems.

These sleep problems are respiratory and tend to waken the patient inopportunely.

They are for example apnoeas, hypopnoeas, acoustic vibrations or snores, or limitation of the respiratory flow, due to a narrowing of the upper airways of the patient.

The document U.S. Pat. No. 5,458,137 describes a method and a device for controlling respiration in the case of sleep problems, which use multiple and variable pressure levels.

A pressure source supplies a breathable gas compressed at a relatively low pressure to the airways of the user.

Pressure sensors monitor the pressures and convert them into electrical signals.

The electrical signals are filtered and processed in order to extract specific characteristics such as the duration and energy levels.

If these characteristics exceed chosen duration and energy level thresholds beyond a minimum time period, the microprocessor indicates the presence of a sleep respiratory problem.

If a chosen number of these events appears during a chosen time period, the microprocessor adjusts the pressure supplied by the source.

The document U.S. Pat. No. 5,490,502 describes a method and an apparatus for optimizing the controlled positive pressure in order to minimize the air flow coming from a generator while ensuring that flow limitation in the airways of the patient does not take place.

Provision is made therein to detect flow limitation by analysing a respiratory flow wave.

As soon as the presence of a flow limitation has been analysed, the system determines an action to be performed for adjusting the controlled positive pressure.

The pressure is increased, reduced or maintained depending on whether flow limitation has been detected and according to the previous actions implemented by the system.

The documents U.S. Pat. No. 5,335,654, EP-A-661 071 and EP-A-651 971 should also be cited.

BRIEF SUMMARY OF THE INVENTION

The invention aims to improve the methods and devices of the state of the art, to automatically and continuously adapt the delivered pressure to the state of the patient and to anticipate and prevent the appearance of problems.

A first object of the invention is a method of controlling an apparatus for supplying air pressure to a patient suffering from sleep problems such as apnoeas.

A second object of the invention is an apparatus for supplying air pressure to a patient suffering from sleep problems such as apnoea, implementing the supply method.

The patient wears a mask by means of which air under pressure is supplied to his upper airways by the apparatus.

According to the invention, a control algorithm is provided using an output flow signal from the apparatus for detecting apnoea, hypopnoea, flow limitation events and leakages, and using the analysis of an item of pressure information for determining the presence of snoring, also referred to as acoustic vibrations.

The pressure supplied to the upper airways of the patient by the apparatus can be maintained constant, be increased or reduced according to the determination of the event which has been performed by the control algorithm.

Thus, if no respiration is detected by the control algorithm within a predetermined minimum time depending on a calculated mean respiration time, the presence of an apnoea is determined.

This predetermined minimum apnoea detection time is for example equal to a time constant, for example 10 seconds, added to a proportionality factor multiplied by the calculated mean respiration time, this factor being for example equal to $5/8$.

For each apnoea, the output flow signal is amplified and filtered in order to determine the presence or absence of cardiac oscillations.

If cardiac oscillations were detected during the last elapsed time interval, for example equal to 5 seconds, then the apnoea is classified as being central and no control takes place in the algorithm.

If no cardiac oscillation was detected in this time interval, the apnoea is classified as being obstructive, and the pressure is increased by a predetermined value a first time and, during the same apnoea, twice more regularly, for example every 15 seconds.

The control algorithm compares peak-to-peak flow variations during the latest respiration of the patient with respect to a predetermined number of previous respirations, for example equal to 8.

After each respiration, a classification is performed into:
normal respiration, if the last peak-to-peak flow value is within a given range with respect to the mean value over the previous 8 respirations, for example from 40% to 150% or 140% thereof;
hypopnoeic respiration, if the last flow value is below this range;
hyperpnoeic respiration, if the last flow value is above this range.

A hypopnoea determination is made if hypopnoeic respiration detection takes place during at least a given time, for example 10 seconds, and terminates after a given number of normal or hyperpnoeic respirations, for example equal to 2.

A hypopnoea determination causes a given increase in pressure, for example 1 cm H2O first, and then, during the same hypopnoea, an increase in pressure by another given value, regularly, for example 0.5 cm H2O every two hypopnoeic respirations.

The control algorithm analyses and compares, respiration by respiration, the waveform of the respiratory flow with a sinusoidal waveform of the same period and same gradient.

After the comparison based on two flow form criteria, each respiration is first classified as normal, intermediate or limited flow.

A final classification, based on the combination of the flow classification and the occurrence of snores, changes the classification of respirations from normal into intermediate, respectively from intermediate into limited flow respiration.

Processing is decided upon when a certain number, for example 2, of successive limited flow respirations or a certain number, for example 5, of successive intermediate respirations take place after for example two normal respirations.

This processing causes a given increase in pressure, repeated regularly a certain number of times, for example 0.3 cm H2O three times every two respirations.

For each respiration, the pressure signal is amplified and filtered in order to detect the presence or absence of acoustic vibrations or snoring.

A determination of a valid snore is made by the control algorithm if the detected acoustic vibration occurred at least for a certain time, for example 7% of the mean duration of the last three respirations, and with a period less than a factor proportional to this mean time, for example 120% thereof.

In the case of a valid snore, the algorithm increases the pressure by a given value, for example 1 cm H2O, if the last control due to a snore took place more than a given time previously, for example 1 minute.

A mean leakage is determined as being equal to the mean flow during respiration.

The control algorithm continuously compares the current leakage with a leakage limit, it being possible to regulate said limit from the pressure.

If the current leakage exceeds the limit, all pressure increase controls generated following event detections are disabled.

After detection of an apnoea or a snoring event or a hypopnoea control or a processing decision, the algorithm will reduce the pressure by a given value, for example 0.5 cm H2O, in a first step after a given time, for example 5 minutes, and regularly for the following reductions, for example every minute.

A given maintenance pressure, for example 8 cm H2O, is supplied by the apparatus if no respiration has been detected during a given time, for example two minutes, or if the pressure supplied has been greater than or equal to a given value for a given time, for example 17 cm H2O for 10 or 30 minutes.

One advantage of the method is an automatic adaptation of the detection criteria to the respiratory characteristics of the patient.

Thus, any modification of the respiratory rhythm is taken into account by the algorithm for performing the detection.

The fact of involving a mean value of respiratory cycle time over a certain number of previous respiratory cycles has the effect of variations in the cycle and respiratory amplitude being tracked regularly and better detection.

The invention will be better understood from a reading of the following description, given with reference to the figures.

DETAILED DESCRIPTION OF THE INVENTION

Figure 1:
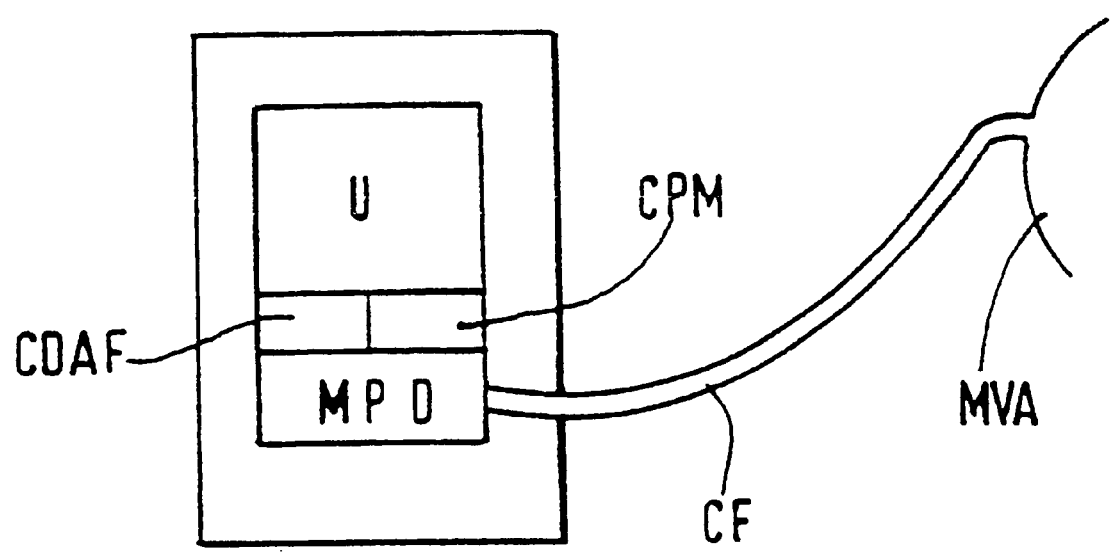
FIG. 1 is a diagram showing the apparatus for supplying air pressure to the patient.

In FIG. 1, the apparatus for supplying air pressure to a patient has a central processing and pressure control unit U, a controlled pressure supply module MPD, a mask MVA for the upper airways of the patient, and a tube CF for supplying air pressure from the module MPD to the mask MVA.

The air flow supplied to the patient and the air pressure prevailing in the mask MVA are measured by means of a supplied air flow sensor CDAF, connected to the central unit U, and by means of a sensor CPM of pressure in the mask MVA, connected to the central unit U.

It is determined from the measured variables whether or not events representing sleep problems appear.

The algorithms of the method according to the invention are implemented by software integrated in the central unit U.

Figure 2:
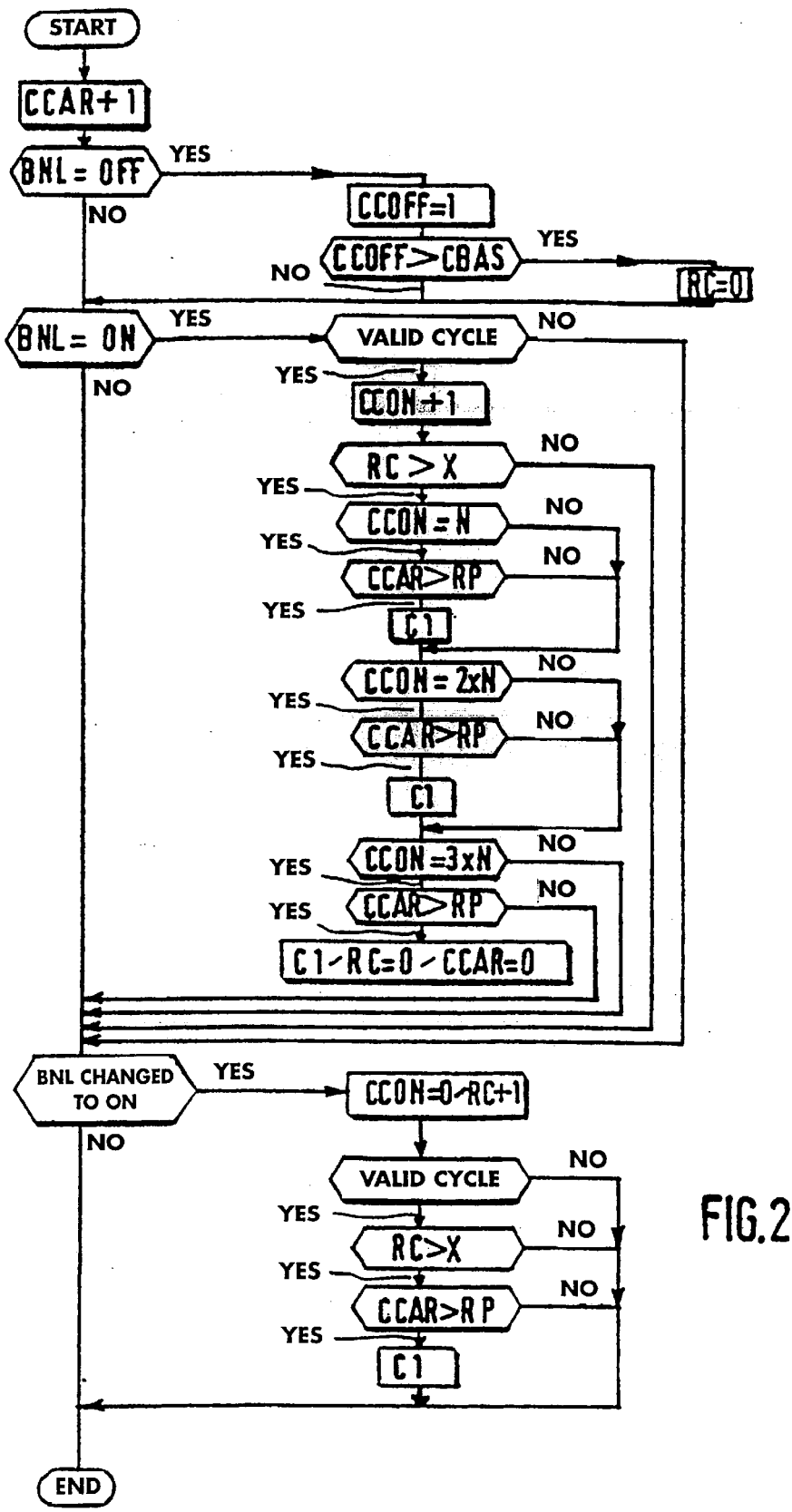
FIG. 2 depicts an algorithm for taking a decision with a view to a first pressure increase control.

In FIG. 2, it is determined from the measured variables whether the current respiratory cycle of the patient corresponds to a predetermined valid respiratory cycle.

A problem appearance indicator BLN is set to a first problem appearance state ON, if the appearance of one or more of the events representing sleep problems is determined.

The indicator BLN is set to a second problem absence state OFF, if the appearance of events representing sleep problems is not determined.

A count is made of a first number CCAR of valid respiratory cycles determined since the last pressure control.

A count is made of a second number CCON of valid respiratory cycles determined since the last change of the indicator BLN to the first state ON.

A count is made of a third number RC of successive changes of the indicator BLN from the second state OFF to the first state ON.

When the indicator BLN is in the first state ON, a first given increase of supplied air pressure is controlled, by means of the control C1, when all the following are true:
  the current respiratory cycle has been determined as being valid;
  the first number CCAR is greater than a first predetermined integer number RP;
  the second number CCON corresponds to one or more other second predetermined integer numbers N;
  the third number RC is greater than or equal to a third predetermined integer number X.

When the indicator BLN changes from the second state OFF to the first state ON, the first given increase of supplied air pressure is controlled, by means of the control C1, when, solely all the following are true:
  the current respiratory cycle has been determined as being valid;

the first number CCAR is greater than a first predetermined integer number RP;

the third number RC is greater than or equal to a third predetermined integer number X.

In one embodiment, the second integer numbers N are between 1 and 300.

In another embodiments the second integer numbers N are the first three multiples of a given integer $N_0$.

In another embodiment, the second integer numbers N are respectively 2, 4 and 6, $N_0$ being equal to 2.

In another embodiment, the first predetermined integer number RP is between 1 and 255.

In another embodiment, the first predetermined integer number RP is equal to 10.

In another embodiment, the third predetermined integer number X is between 1 and 100.

In another embodiment, the third predetermined integer number X is equal to 1.

In another embodiment, the first given pressure increase control C1 is less than +10 mbar.

In another embodiment, the first given pressure increase control C1 is substantially equal to +0.3 mbar.

The first and third numbers CCAR; RC of counted valid respiratory cycles and counted changes are reset to 0, after the second counted number CCON of valid cycles has reached the largest of the second predetermined integer numbers N.

The second counted number CCON is reset to 0 when the indicator BLN changes from the second state OFF to the first state ON.

The predetermined valid respiratory cycle corresponds to a maximum respiratory flow greater than a predetermined flow value such as 50 ml/s, an inspiratory volume greater than a predetermined volume value such as 0.05 liters and an absence of saturation at flow detection time.

Figure 3:
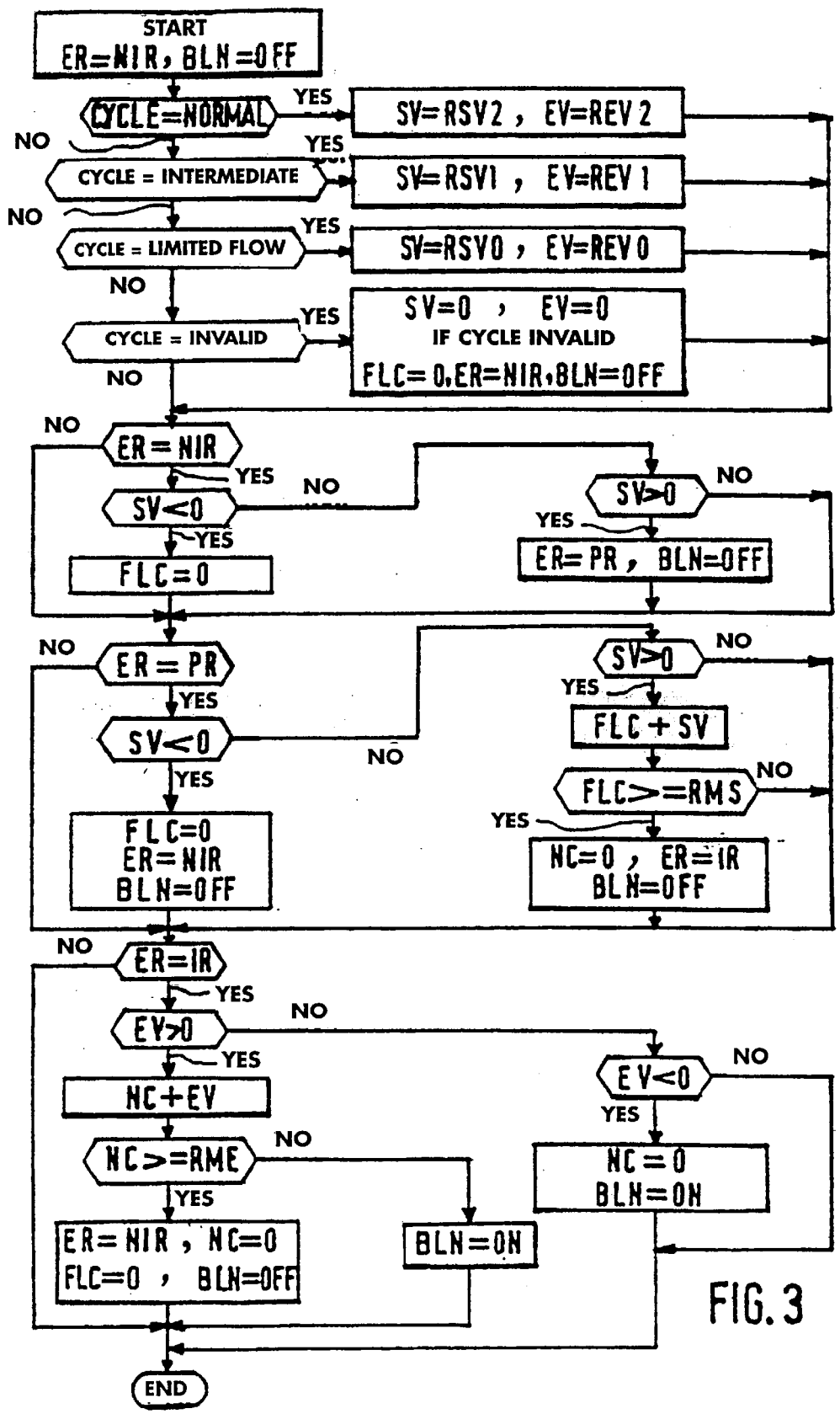
FIG. 3 depicts an algorithm for indicating the appearance of problems.

In FIG. 3, in order to give the state ON or OFF to the problem appearance indicator BLN, when the apparatus is started up, a state variable ER is initialized to a third processing absence state NIR and the indicator BLN is initialized to the second state OFF.

Then, sequentially, from the measured variables, the respiratory cycles are designated as belonging to different categories such as limited flow cycle, intermediate cycle, normal cycle and invalid cycle, each corresponding respectively to weightings RSV0, REV0; RSV1, REV1; RSV2, REV2; 0,0;

the weightings of the category of the currently designated cycle are assigned to first and second weighting accumulators SV; EV;

if the designated cycle belongs to the invalid cycle category, the state variable ER is reset to the third state NIR and the indicator BLN is reset to the second state OFF and a first counter FLC is initialized to a predetermined value.

If the state of the state variable ER corresponds to the third state NIR:

if the value of a first accumulator SV is less than a first comparative value, the counter FLC is reinitialized to its predetermined value;

if the value of the first accumulator SV is substantially equal to its first comparative value, no action is taken and the next test is passed to;

if the value of the first accumulator SV is greater than its first comparative value, the state variable ER is changed to a fourth processing possibility state PR and the indicator BLN is set to the second state OFF.

If the state of the state variable ER corresponds to the fourth state PR and if the value of the first accumulator SV is less than its first comparative value, the first counter FLC is reinitialized to its predetermined value, and the state variable ER and the indicator BLN are reset respectively to the third and second states NIR; OFF;

if the value of the first accumulator SV is substantially equal to its first comparative value, no action is taken and the next test is passed to;

if the value of the first accumulator SV is greater than its first comparative value, the first counter FLC is made to take its previous value with the value of the first accumulator SV added to it, and if then the value of the first counter FLC is greater than or equal to a predetermined high stop RMS:

a second counter NC is reinitialized to a predetermined value;

the state variable ER is changed to a fifth processing state IR; and the indicator BLN is changed to the first state ON.

If the state of the state variable ER corresponds to the fifth processing state IR:

if the value of the second accumulator EV is greater than a second comparative value, the second counter NC is made to take its previous value with the value of the second accumulator EV added to it, and if then the value of the second counter NC is greater than or equal to a low stop RME, the state variable ER and the indicator BLN are reset respectively to the third and second states NIR; OFF and the first and second counters FLC; NC are reinitialized to their predetermined respective values;

or otherwise, the indicator BLN is changed to its first state ON;

if the value of the second accumulator EV is less than its second comparative value, the second counter NC is reinitialized to its predetermined respective value and the indicator BLN is changed to the first state ON;

if the value of the second accumulator EV is substantially equal to its second comparative value, no action is taken.

In one embodiment, the weightings RSV2, REV2; RSV1, REV1; RSV0, REV0; 0,0 corresponding to the normal cycle, intermediate cycle, limited flow cycle and invalid cycle categories, are respectively substantially equal to −1; 1; 5 and 0 for the first accumulator SV and are respectively substantially equal to 1; −1; −1 and 0 for the second accumulator EV.

The first and second comparative values and the predetermined initialization values of the first and second counters FLC; NC are each substantially equal to 0.

The high and low stops RMS; RME are respectively substantially equal to 10 and 2.

Figure 4:
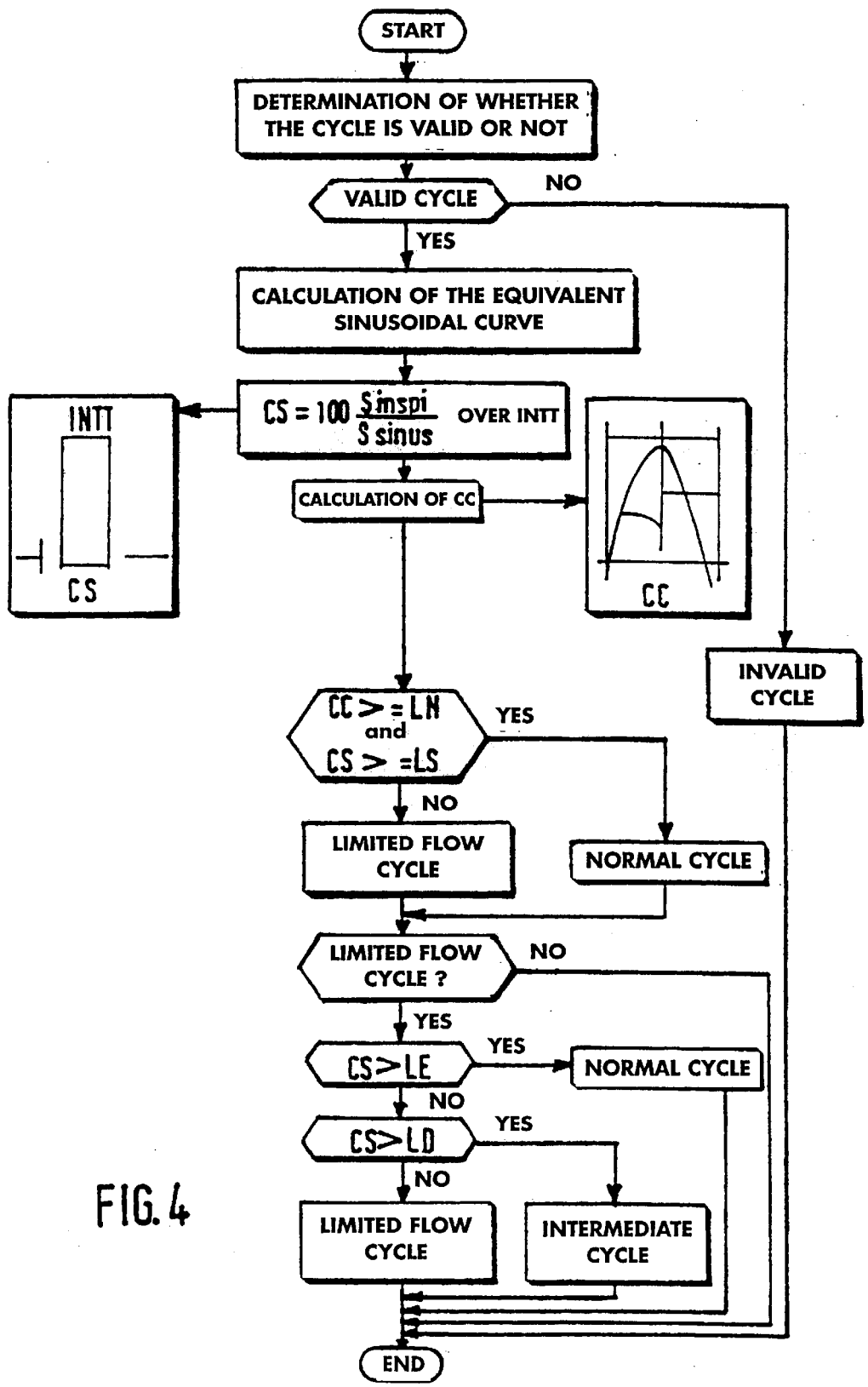
FIG. 4 depicts a respiration designation algorithm.

In FIG. 4, the measured respiratory cycles are designated.

The predetermined valid respiratory cycle corresponds to a maximum inspiratory flow greater than a predetermined flow value such as 50 ml/s, an inspiratory volume greater than a predetermined volume value such as 0.05 liters, an absence of saturation at flow detection time, a measured inspiratory time within a predetermined interval such as 0.5 seconds to 6 seconds and a measured respiratory cycle duration within another predetermined interval such as 1.5 seconds to 20 seconds.

If the measured respiratory cycle is determined as being valid, then
- a calculation is made of an equivalent sinusoidal curve meeting predetermined characteristics with respect to the inspiratory curve of the measured inspiratory cycle;
- a calculation is made of a surface criterion CS proportional to the ratio of the area delimited by the inspiratory curve to the area delimited by the equivalent sinusoidal curve, each being taken over the same time interval, within the inspiratory phase of the measured respiratory cycle;
- a calculation is made of a criterion of correlation CC between the inspiratory curve of the measured inspiratory cycle and the equivalent sinusoidal curve;
- if the calculated correlation criterion CC is greater than or equal to a first predetermined normal limit LN, and if the calculated surface criterion CS is greater than a second predetermined surface limit LS, the measured respiratory cycle is designated as normal and otherwise, it is designated as a limited flow cycle.

If the measured respiratory cycle was designated as a limited flow cycle,
- if the calculated surface criterion CS is greater than a third predetermined expert limit LE, the measured respiratory cycle is redesignated as normal,
- or otherwise,
- if the calculated surface criterion CS is greater than a fourth predetermined flow limit LD, the measured respiratory cycle is redesignated as intermediate,
- and in the contrary case, it is designated as a limited flow cycle.

The second surface limit LS, the fourth flow limit LD and the third expert limit LE are predetermined in an ascending order.

The predetermined characteristics of the equivalent sinusoidal curve comprise a half period substantially equal to the measured inspiratory time and a gradient at the origin substantially equal to that of the inspiratory curve when it reaches substantially one third of its maximum amplitude.

In one embodiment, the calculated surface criterion CS is substantially equal to one hundred times the ratio of the areas each taken from substantially one quarter to three quarters of the duration of the inspiratory phase of the measured respiratory cycle.

The calculated correlation criterion CC is substantially equal to the maximum of one hundred times the coefficients of correlation between the inspiratory curve and the equivalent sinusoidal curve taken respectively over the second half of the inspiratory phase and over the whole thereof.

The first, second, fourth and third limits LN; LS; LD; LE are respectively between 45 and 100; 0 and 100; 0 and 100; 0 and 100 and are for example substantially equal to 87; 40; 60 and 90 respectively.

Figure 5:
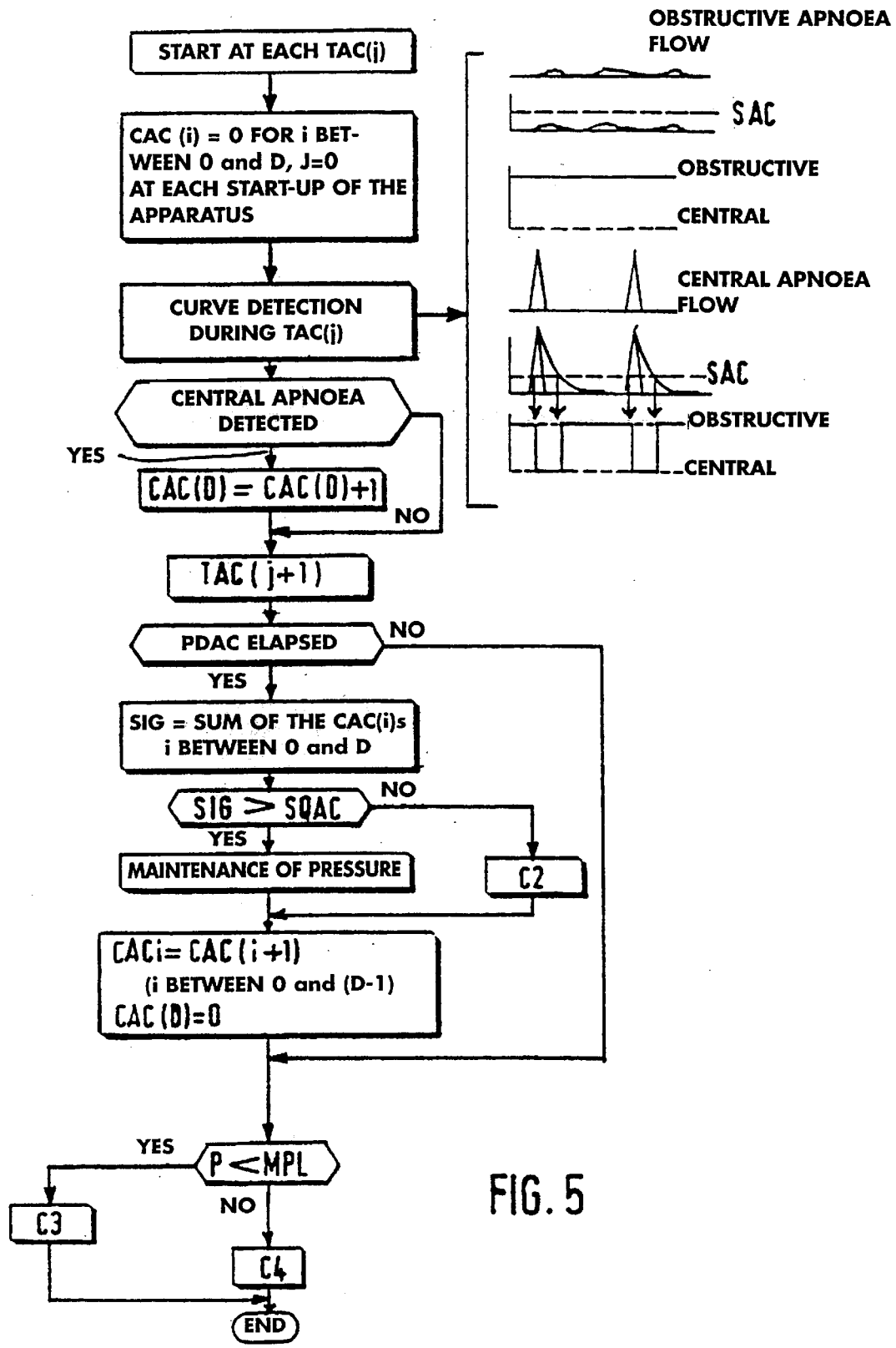
FIG. 5 depicts an algorithm for detecting central and obstructive apnoea and for pressure control according to the result of these detections, as well as an algorithm for reducing pressure according to the previous appearance or not of events representing sleep problems.
Figure 6:
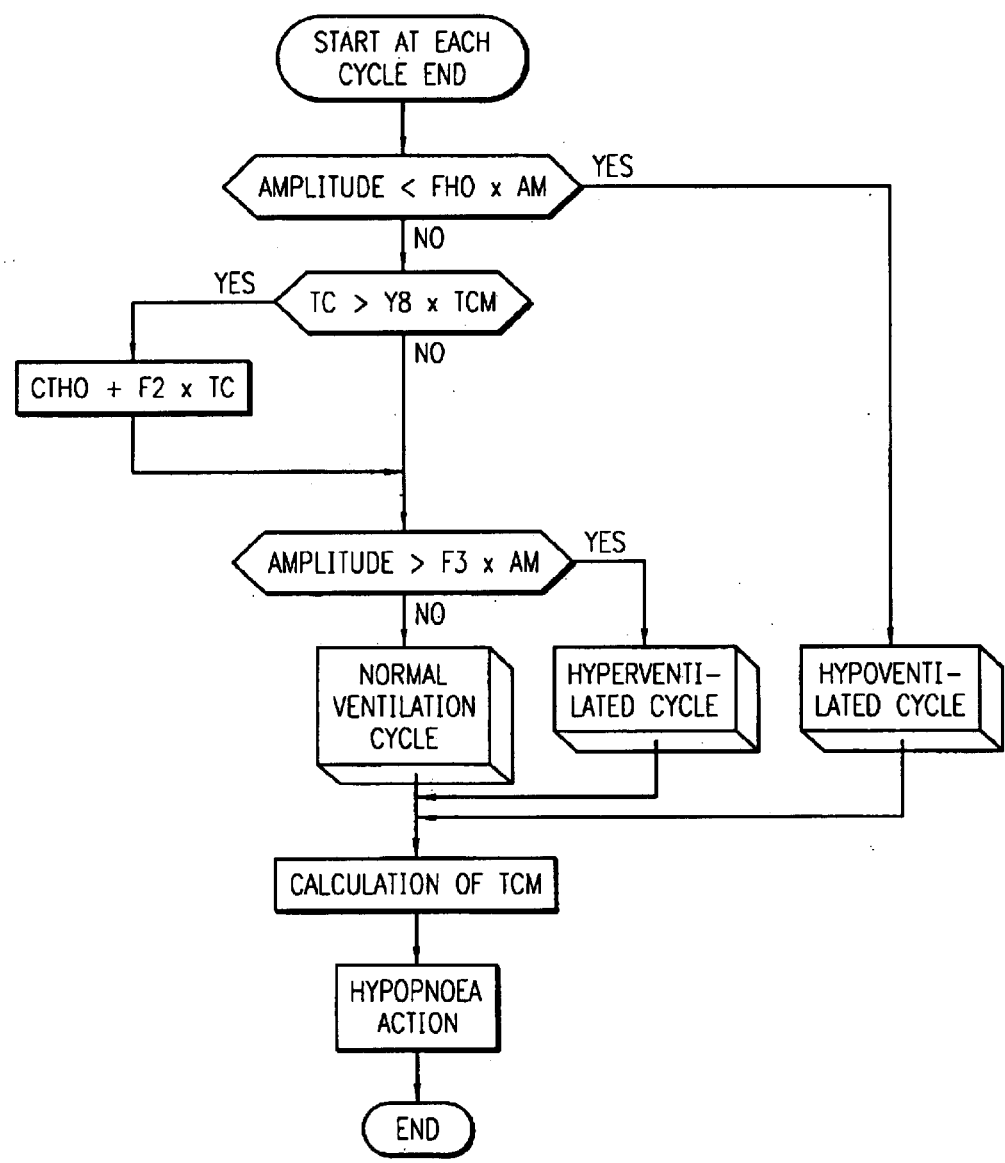
FIG. 6 depicts an algorithm for designating cycles as normal ventilation, hyperventilation or hypoventilation.

In FIG. 5, obstructive apnoeas and central apnoeas are detected.

The algorithm depicted in FIG. 5 is performed during each of a number (NINT) of predetermined consecutive time intervals TAC(j).

The predetermined consecutive time intervals TAC(j) are those within a predetermined apnoea detection period PDAC.

In this algorithm, there are detected, for example by hardware means such as analogue or digital filters, the oscillations of the measured flow curve, which are of frequencies within a frequency range P2.

Then it is detected whether the amplitude of the detected oscillations of the measured flow curve goes successively above and then below a first predetermined central apnoea threshold SAC or whether this amplitude remains less than the first central apnoea threshold SAC, as depicted schematically at the right of FIG. 5 by:
- the behaviour of an obstructive apnoea flow curve (curve constantly below the first threshold SAC);
- the behaviour of a central apnoea flow curve (curve going a number of times successively above and then below the first threshold SAC).

In the presence of at least one detection of a passage above and then below the first threshold SAC, a central apnoea detection CAC(D) is counted.

Then, at each apnoea detection period PDAC,
- the sum SIG is performed of the numbers CAC(i) of central apnoea detections counted, successively over the last (D+1) apnoea detection periods;
- a second predetermined increase of delivered air pressure is controlled C2 if the sum SIG of the numbers CAC(i) of counted detections is less than or equal to a second predetermined central apnoea designation threshold SQAC;
- a maintenance of delivered air pressure is controlled, if the sum SIG of the numbers CAC(i) of counted detections is greater than the second threshold SQAC.

In one embodiment, the second central apnoea designation threshold SQAC is between 0 and 50, and is for example substantially equal to 10.

The predetermined consecutive time intervals TAC(j) correspond to ten (NINT) consecutive time intervals each of substantially 100 ms, the apnoea detection period PDAC corresponding substantially to 1 second.

The second pressure increase control C2 is between 1 and 10 mbar and is for example substantially equal to +1 mbar.

The number (D+1) of apnoea detection periods PDAC, over which the sum of the counted central apnoea detection numbers CAC(i) is performed, is substantially equal to 5.

The second oscillation frequency range P2 is between substantially 2.5 and 47 Hz.

The counted central apnoea detection numbers CAC(i) are reset to 0 when the apparatus is started up.

FIG. 5 also depicts an algorithm for pressure reduction according to the previous appearance or not of events representing sleep problems.

According to this algorithm, depicted at the bottom of FIG. 5, the measured pressure P is compared with a predetermined pressure value MPL.

After determination of the appearance of one or more events,
- if the measured pressure P is less than the predetermined value MPL, a third predetermined pressure reduction control C3 is performed;
- if the measured pressure P is greater than or equal to the predetermined value MPL, a fourth predetermined pressure reduction control C4 is performed;
- then, if no event appearance has been detected after one or more of the pressure reduction controls C3; C4, the fourth predetermined pressure reduction control C4 is performed.

The fourth pressure reduction control C4 is such that it causes a greater pressure reduction per unit of time than that caused by the third control C3.

In one embodiment, the fourth pressure reduction control C4 is substantially −0.5 mbar/1 minute and the third pressure reduction control C3 is substantially −0.5 mbar/5 minutes, the comparative pressure value MPL is between 4 and 19 mbar and is for example substantially equal to 17 mbar.

This algorithm for pressure reduction according to the appearance or not of events is implemented after the one for central and obstructive apnoea detection as depicted in FIG. 5 but is also implemented, in non-depicted embodiments, after the other algorithms such as:

the one for processing decision taking, when the indicator BLN has changed from the first state ON to the second state OFF;

the one for hypopnoeic respiration detection described below;

the one for acoustic vibration detection described below.

In FIGS. 6 to 9, the respiratory cycles are designated as hyperventilated, hypoventilated or normal ventilation cycles and pressure controls are generated according to the designations made.

At each measured respiratory cycle end, the mean amplitude AM over a fourth predetermined number Y4 of previous respiratory cycles is calculated.

Figure 7:
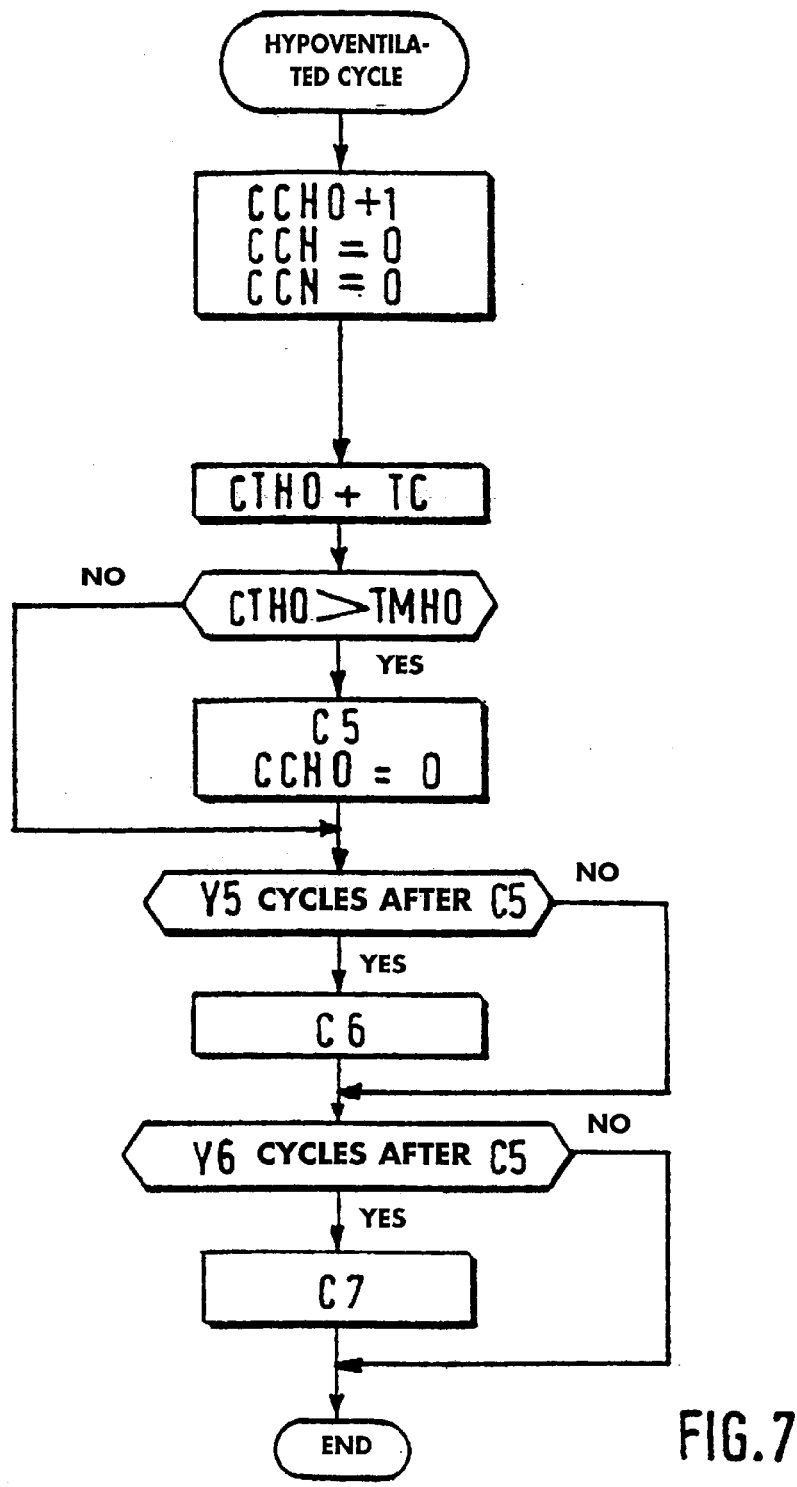
FIG. 7 depicts a hypopnoeic respiration detection algorithm.

As depicted in FIG. 7, if the measured amplitude of the last respiratory cycle is less than the calculated mean amplitude AM multiplied by a first predetermined hypopnoea factor FHO, then the duration TC of the last measured respiratory cycle is added to a hypopnoea time counter CTHO, if the current value of the hypopnoea time counter CTHO is greater than or equal to a minimum hypopnoea time TMHO, a fifth predetermined pressure increase is controlled by means of a control C5;

after the end of a fifth predetermined number Y5 of respiratory cycles following the fifth pressure increase control C5, a sixth predetermined pressure increase is controlled C6;

after the end of a sixth predetermined number Y6 of respiratory cycles, greater than the fifth number Y5, following the fifth pressure increase control C5, a seventh pressure increase is controlled by means of a control C7.

The hypopnoea time counter CTHO is initialized to 0 when the apparatus is started up.

In one embodiment, the fourth given number Y4 of respiratory cycles for mean amplitude calculation is substantially equal to 8.

The first predetermined hypopnoea factor FHO is between 1 and 100% and is for example substantially equal to 40%.

The minimum hypopnoea time TMHO is between 1 second and 25 seconds and is for example substantially equal to 10 seconds.

The fifth and sixth predetermined numbers Y5;, Y6 of respiratory cycles are substantially equal to respectively 2 and 4.

The fifth predetermined pressure increase C5 is between 0.1 mbar and 10 mbar and is for example substantially equal to +1 mbar.

The sixth and seventh predetermined pressure increases C6; C7 are each less than the fifth control C5 and are for example each substantially equal to half the fifth pressure increase C5.

Figure 8:
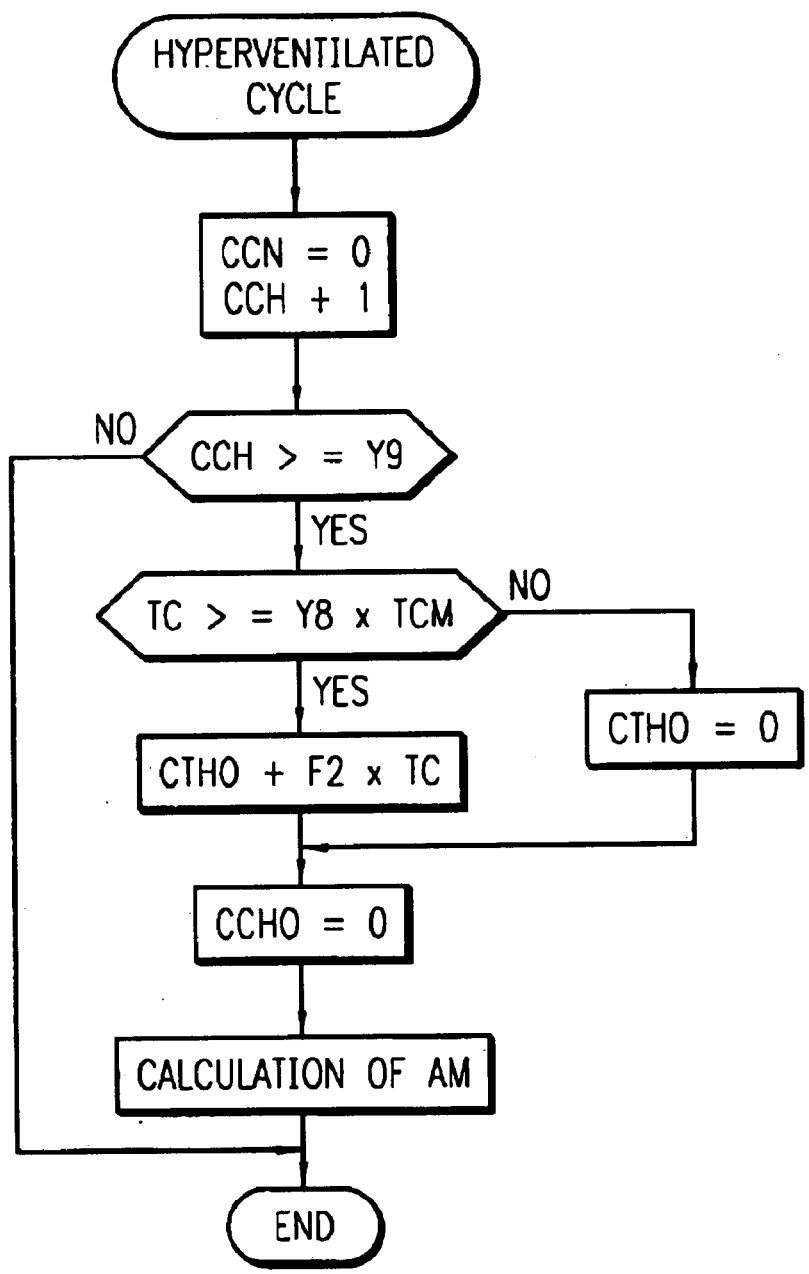
FIG. 8 depicts a hyperpnoeic respiration detection algorithm.
Figure 9:
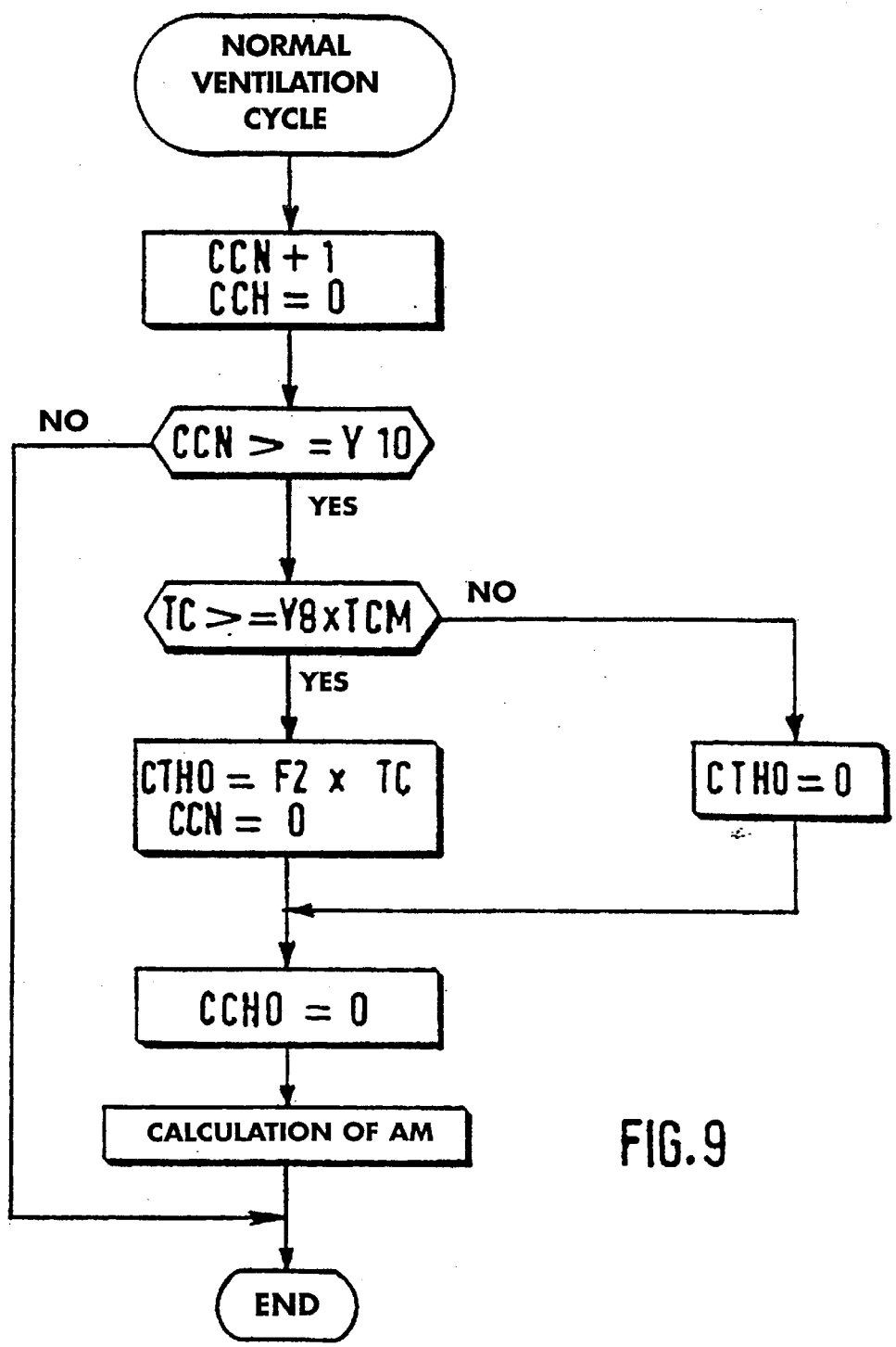
FIG. 9 depicts a normal respiration detection algorithm.

As depicted in FIGS. 8 and 9, if the measured amplitude of the last respiratory cycle is greater than or equal to the calculated mean amplitude AM multiplied by the first hypopnoea factor FHO, then the mean respiratory cycle time TCM over a seventh predetermined number Y7 of previous cycles is calculated.

If the measured duration TC of the last cycle is greater than an eighth predetermined number Y8 multiplied by the calculated mean respiratory cycle time TCM, the measured duration TC of the last cycle, multiplied by a second hypopnoea factor F2, is added to the hypopnoea time counter CTHO.

If the measured amplitude of the last measured respiratory cycle is greater than a third hyperventilation factor F3, greater than the first hypopnoea factor FHO, multiplied by the calculated mean amplitude AM, the last cycle is designated as hyperventilated, a hyperventilated cycle counter CCH is incremented by one unit, a normal ventilation cycle counter CCN is reset to 0 and if the value of the hyperventilated cycle counter CCH is greater than or equal to a ninth predetermined number Y9, if the duration of the last cycle TC is greater than or equal to the eighth number Y8 multiplied by the calculated mean cycle time TCM, the second factor F2 multiplied by the duration of the last respiratory cycle TC is added to the hypopnoea time counter CTHO;

and otherwise, the hypopnoea time counter CTHO is reset to 0;

then a hypoventilated cycle counter CCHO is reset to 0 and the mean respiratory cycle amplitude AM over the predetermined number Y4 of previous respiratory cycles is calculated.

If the measured amplitude of the last measured respiratory cycle is less than or equal to the third factor F3 multiplied by the calculated mean amplitude AM, the last cycle is designated as a normal ventilation cycle, the hyperventilated cycle counter CCH is reset to 0 and the normal ventilation cycle counter CCN is incremented by one unit, and if the value of the normal ventilation cycle counter CCN is greater than or equal to a tenth predetermined number Y10, if the duration of the last cycle TC is greater than or equal to the eighth number Y8 multiplied by the calculated mean cycle time TCM, the second factor F2 multiplied by the duration of the last cycle TC is assigned to the hypopnoea time counter CTHO and the normal ventilation cycle counter CCN is reset to 0, and otherwise, the hypopnoea time counter CTHO is reset to 0;

then the hypoventilated cycle counter CCHO is reset to 0 and the mean amplitude of the respiratory cycle over the predetermined number Y4 of respiratory cycles is calculated.

In one embodiment, the second factor F2 is substantially equal to ⅝.

The third hyperventilation factor F3 is between 100% and 200% and is for example substantially equal to 140%.

The seventh, eighth, ninth and tenth predetermined numbers Y7; Y8; Y9; Y10 are respectively substantially equal to 3; 2; 2; and 2.

Figure 10:
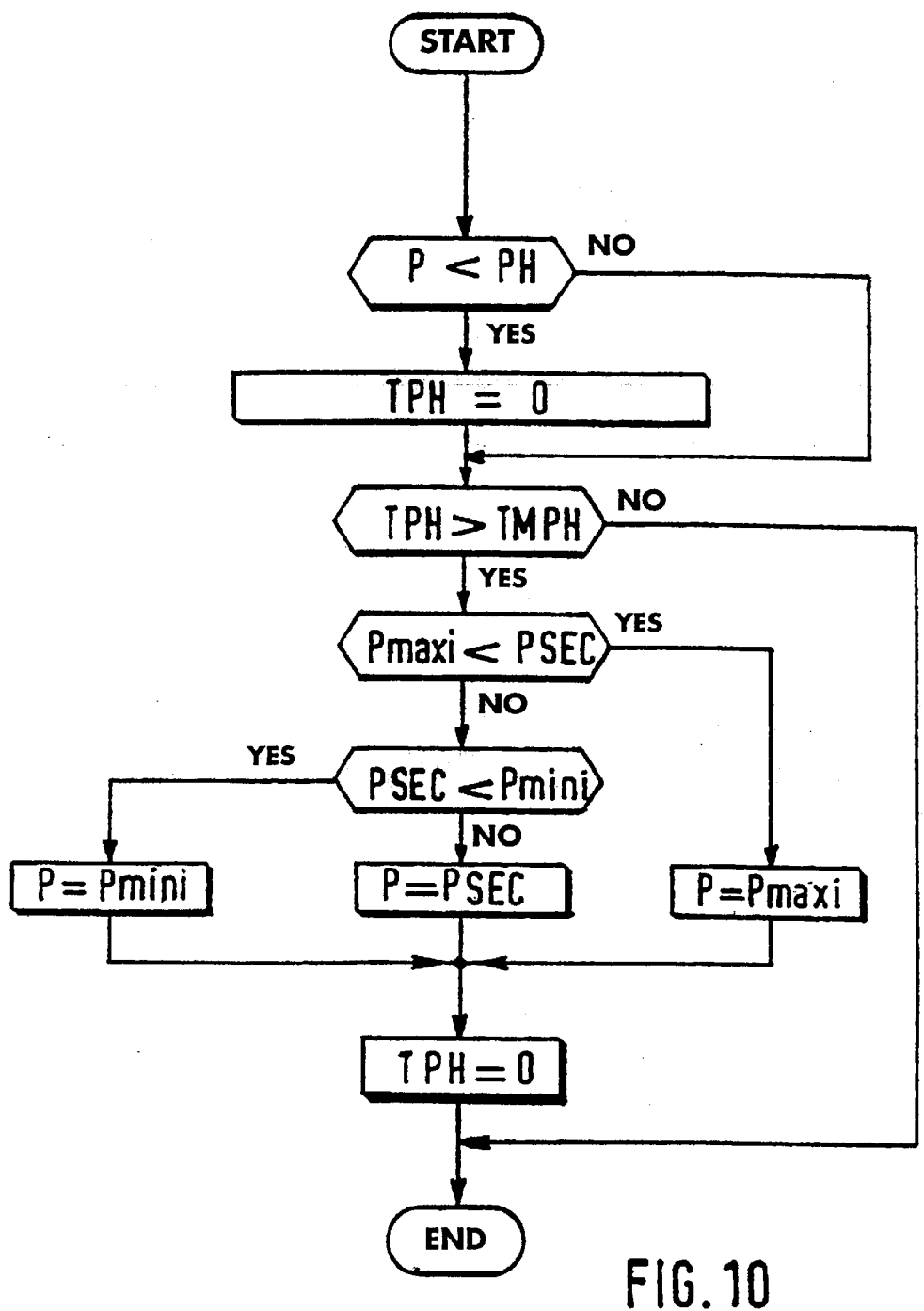
FIG. 10 depicts a high pressure detection algorithm.

In FIG. 10, it is detected whether the pressure is too high.

If the measured pressure P is less than a predetermined high pressure value PH, a high pressure time counter TPH is reset to 0.

If the value of the high pressure time counter TPH is greater than a maximum high pressure time TMPH and if the maximum regulated pressure value Pmaxi is less than a predetermined safety pressure value PSEC, the pressure P is controlled to this maximum regulated pressure value Pmaxi;

if the minimum regulated pressure value Pmini is greater than a predetermined safety pressure value PSEC, the pressure P is controlled to this minimum regulated pressure value Pmini;

if the previous two conditions are not fulfilled, the pressure P is controlled to the safety pressure value PSEC. then the high pressure time counter TPH is reset to 0.

In one embodiment, the high pressure value PH is between 10 mbar and 25 mbar and is for example substantially equal to 17 mbar.

The maximum high pressure time TMPH is between 1 and 100 minutes and is for example substantially equal to 10 minutes or 30 minutes.

The safety pressure value PSEC is substantially equal to 8 mbar.

Figure 11:
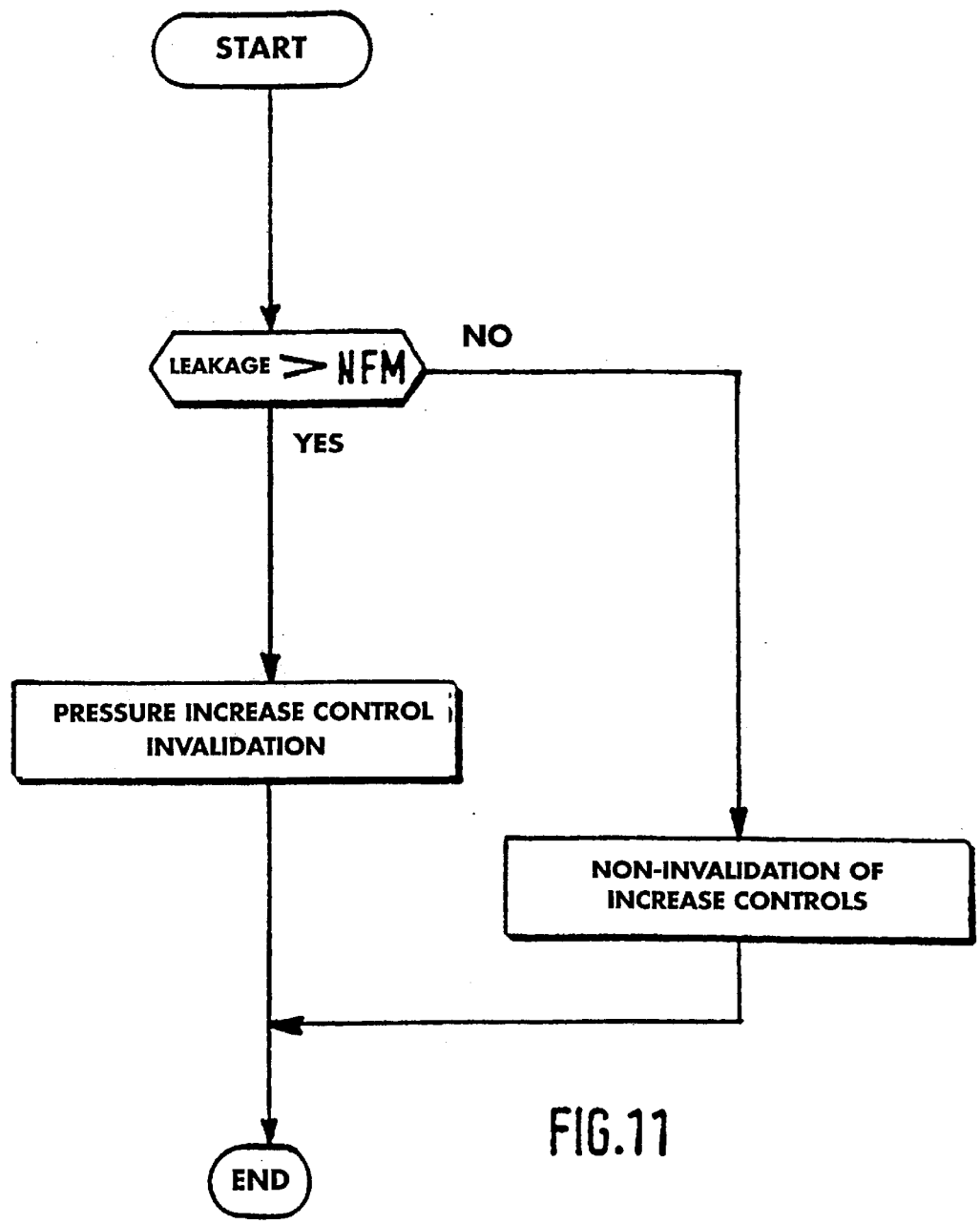
FIG. 11 depicts a mask leakage detection algorithm.

In FIG. 11, an air leakage is measured, substantially equal to the mean flow during respiration of the patient.

If the measured air leakage is greater than a predetermined leakage level NFM, the pressure increase controls are invalidated.

In one embodiment, NFM=A×Pfiltered+B.

According to this formula, the predetermined leakage level NFM is substantially equal to a leakage coefficient A multiplied by a filtered air pressure in the mask, added to an additive leakage coefficient B, the leakage coefficient A being between 0 and 10 liters/minute.mbar and being for example substantially equal to 2.5 liters/minute.mbar.

The additive leakage coefficient B is between 0 and 100 liters/min and is for example substantially equal to 50 liters/min.

Figure 12:
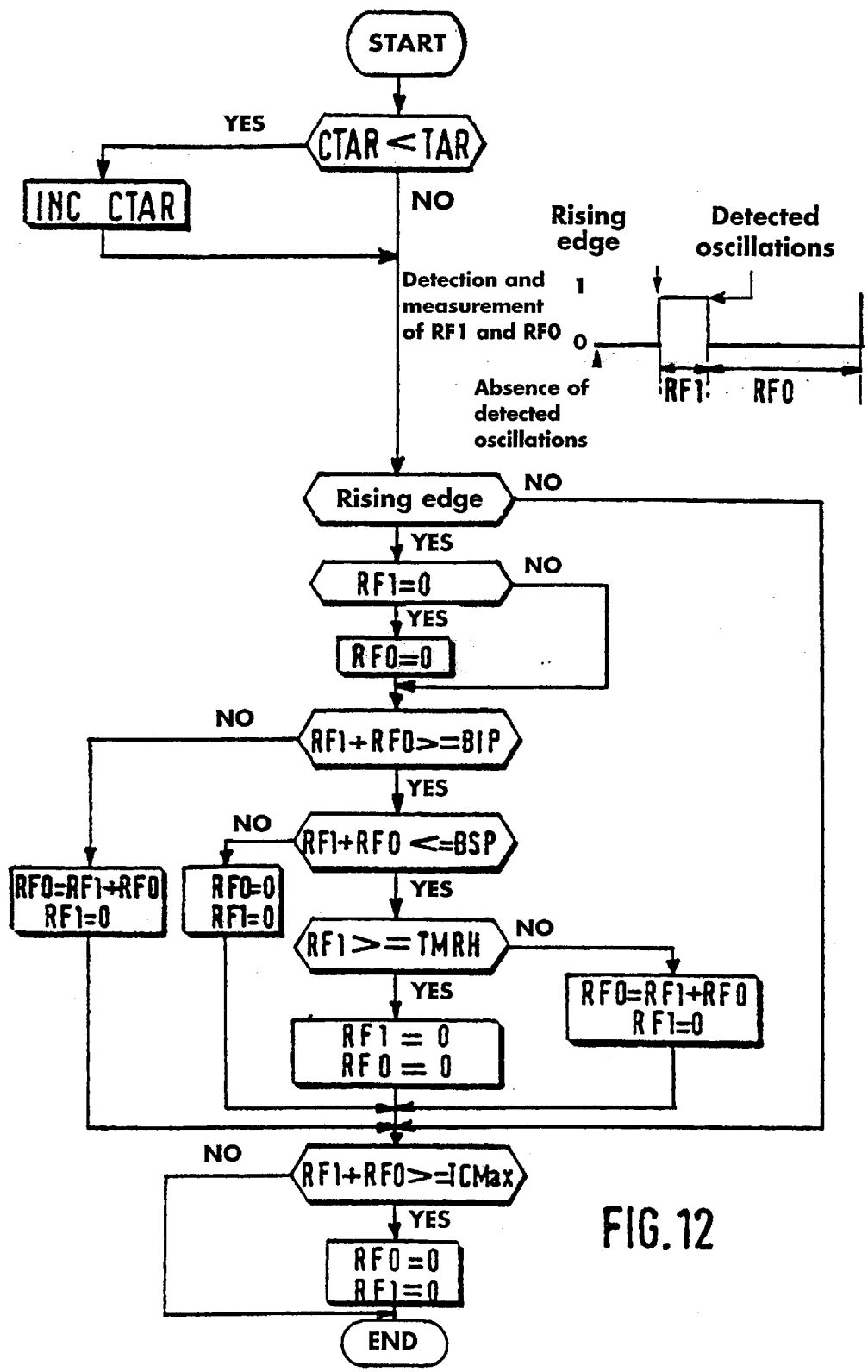
FIG. 12 depicts an acoustic vibration detection algorithm.
Figure 13:
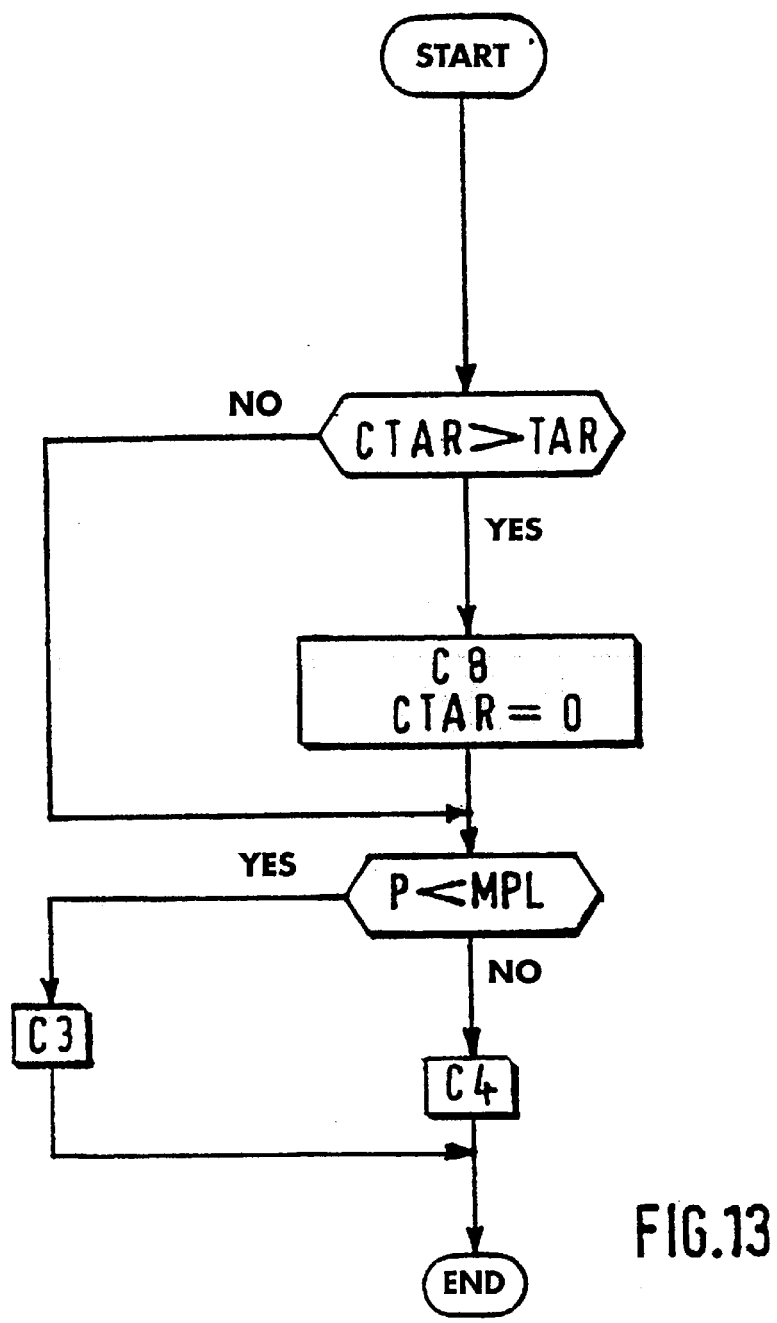
FIG. 13 depicts an algorithm for reducing pressure in the event of acoustic vibration detection.

In FIG. 12, it is detected whether the measured pressure curve has oscillations, such as acoustic vibrations, within a frequency range P1.

This detection is performed for example by hardware means such as analogue or digital filters.

A measurement is made of the detected oscillation presence time RF1 between two successive absences of detected oscillations and the detected oscillation absence time RF0 between two successive presences of detected oscillations.

If the sum of the measured detected oscillation absence and presence times RF0; RF1 is within a prescribed time range BIP; BSP.

If the measured oscillation presence time RF1 is greater than or equal to a minimum oscillation time TMRH and if the value of a counter CTAR of elapsed time since the last but one time that the previous time conditions were fulfilled is greater than a prescribed waiting time TAR, an eighth predetermined pressure increase is controlled C8 and the elapsed time counter CTAR is reset to 0.

The algorithms for acoustic vibration detection and control in the case of acoustic vibrations are implemented at prescribed time intervals, notably regularly and for example every 100 ms.

At the start of the acoustic vibration detection algorithm depicted in FIG. 12, if the value of the elapsed time counter CTAR is less than the prescribed waiting time TAR, this counter is incremented (INC CTAR) by the prescribed time interval mentioned above.

If the sum of the measured detected oscillation presence and absence times RF0; RF1 is below the prescribed time range BIP; BSP or if the measured detected oscillation presence time RF1 is less than the minimum oscillation time TMRH, the measured detected oscillation absence time RF0 is replaced by the sum of the measured detected oscillation absence and presence times RF0; RF1, and then the measured detected oscillation presence time RF1 is reset to 0.

If the sum of the measured detected oscillation absence and presence times RF0; RF1 is above the predetermined time range BIP; BSP or a predetermined maximum time TCMax, each of the measured detected oscillation absence and presence times RF0; RF1 is reset to 0.

If the two conditions mentioned above concerning the sum of the presence and absence times RF1, RF0 and the presence time RF1 are not fulfilled, each of the measured detected oscillation absence and presence times RF0; RF1 is reset to 0.

In one embodiment, the predetermined maximum time TCMax is substantially equal to twice the mean respiratory cycle time TCM over the last three measured cycles.

The prescribed time range BIP; BSP is substantially between 10% and 120% of the calculated mean cycle time TCM.

The minimum oscillation time TMRH is substantially equal to 7% of the calculated mean cycle time TCM.

The prescribed waiting time TAR is between 1 and 30 minutes and is for example substantially equal to 1 minute.

The eighth pressure increase control C8 is between 0.1 mbar and 10 mbar and is for example substantially equal to 1 mbar.

The oscillation detection frequency range P1 is between substantially 30 and 300 Hz.

The chronology of the detected events is stored and the stored chronology is read, for example after one night.

To that end, the central unit U of the apparatus has a memory, not depicted, capable of being written and read with the chronology of the detected events.

This chronology can be displayed, for example on a monitor, by reading the content of the memory, by means of a computer, not depicted.

What is claimed is:

1. A method of controlling an apparatus for supplying air pressure delivered to a patient, comprising:

providing a flow of air at a maintenance pressure to an airway of a patient;

measuring the flow of air to the patient;

detecting the presence of an apnoea in the flow of air to the patient;

detecting oscillations of the measured air flow to the patient;

determining whether an amplitude of the detected oscillations is greater than a first central apnoea threshold;

determining whether an amplitude of the detected oscillations is less than the first central apnoea threshold;

identifying the occurrence of a central apnoea when the amplitudes of the detected oscillations are successively greater than and then less than the first central apnoea threshold;

summing each occurrence of the central apnoeas identified during a ventilation cycle of air flow to the patient;

determining whether the sum of the occurrence of central apnoeas is less than or equal to a second central apnoea threshold during the ventilation cycle;

determining whether the ventilation cycle is a normal cycle; and increasing the pressure of the air flow to the patient above the maintenance pressure when the ventilation cycle is determined to be a normal cycle, the presence of an apnoea is detected and the sum of the occurrence of central apnoeas is less than or equal to the second central apnoea threshold.

2. The method according to claim 1, further comprising:

measuring the pressure of the air flow to the patient;

setting a high pressure time counter to zero when the pressure of the air flow to the patient is less than a high pressure threshold;

incrementing the high pressure time counter when the pressure of the air flow to the patient is not less than the high pressure threshold; and reducing the pressure of the air flow to the patient to a safety pressure value when the value of the high pressure time counter is greater than a maximum high pressure time threshold.

3. The method according to claim 2, further comprising setting the high pressure threshold to between ten mbar and twenty-five mbar, setting the maximum high pressure time threshold to between one minute and one hundred minutes, and setting safety pressure value to about eight mbar.

4. The method according to claim 1, wherein determining whether a ventilation cycle of air flow to the patient is a normal cycle includes calculating a mean amplitude of the flow air to the patient of during the ventilation cycle and includes designating the ventilation cycle as not a normal cycle when the mean amplitude is greater than a first hyperventilation factor.

5. The method according to claim 1, further comprising measuring a leakage of air flow to the patient during the ventilation cycle, and maintaining the level of pressure of the air flow to the patient when the measured air leakage is greater than a leakage level threshold.

6. The method according to claim 5, further comprising setting the leakage level threshold to substantially equal to an additive leakage value summed with a leakage coefficient multiplied by the measured air flow to the patient.

7. The method according to claim 6, further comprising setting the additive leakage coefficient between zero liters/minute and one hundred liters/minute, and setting the leakage coefficient between zero liters/minute-mbar and ten liters/minute-mbar.

8. The method according to claim 1, further comprising analyzing the detected oscillations so as to identify acoustic vibrations within an acoustic frequency range, and increasing the pressure of the air flow to the patient when acoustic vibrations are identified.

9. The method according to claim 8, further comprising setting the acoustic frequency range between about thirty hertz and about three hundred hertz.

10. The method according to claim 1, further comprising storing a chronology of each detected presence of an apnoea in the flow of air to the patients, and reading the stored chronology.

11. A method for supplying air under pressure to a patient, comprising:

providing a flow of air at a pressure to an airway of a patient;

measuring the flow of air to the patient;

measuring the pressure of the air flow to the patient;

detecting the presence of an apnoea in the flow of air to the patient;

detecting oscillations of the measured air flow to the patient;

determining whether an amplitude of the detected oscillations is greater than a first central apnoea threshold;

determining whether an amplitude of the detected oscillations is less than the first central apnoea threshold;

identifying the occurrence of a central apnoea when the amplitudes of the detected oscillations are successively greater than and then less than the first central apnoea threshold;

summing each occurrence of the central apnoeas identified during a ventilation cycle of air flow to the patient;

determining whether the sum of the occurrence of central apnoeas is less than or equal to a second central apnoea threshold during the ventilation cycle;

determining whether the ventilation cycle is a normal cycle, including calculating a mean amplitude of the flow air to the patient of during the ventilation cycle and designating the ventilation cycle as not a normal cycle when the mean amplitude is greater than a first hyperventilation factor;

setting a high pressure time counter to zero when the pressure of the air flow to the patient is less than a high pressure threshold;

incrementing the high pressure time counter when the pressure of the air flow to the patient is not less than the high pressure threshold;

measuring a leakage of air flow to the patient during the ventilation cycle;

increasing the pressure of the air flow to the patient when the ventilation cycle is determined to be a normal cycle, the presence of an apnoea is detected, the sum of the occurrence of central apnoeas is less than or equal to the second central apnoea threshold and the measured air leakage is not greater than a leakage level threshold; and reducing the pressure of the air flow to the patient to a safety pressure value when the value of the high pressure time counter is greater than a maximum high pressure time threshold.

12. The method according to claim 11, further comprising analyzing the detected oscillations so as to identify acoustic vibrations within an acoustic frequency range, and increasing the pressure of the air flow to the patient when acoustic vibrations are identified.

13. An apparatus for supplying air pressure delivered to a patient, comprising:

means for providing a flow of air at a maintenance pressure to an airway of a patient;

means for measuring the flow of air to the patient;

means for detecting the presence of an apnoea in the flow of air to the patient;

means for detecting oscillations of the measured air flow to the patient;

means for determining whether an amplitude of the detected oscillations is greater than a first central apnoea threshold;

means for determining whether an amplitude of the detected oscillations is less than the first central apnoea threshold;

means for identifying the occurrence of a central apnoea when the amplitudes of the detected oscillations are successively greater than and then less than the first central apnoea threshold;

means for summing each occurrence of the central apnoeas identified during a ventilation cycle of air flow to the patient;

means for determining whether the sum of the occurrence of central apnoeas is less than or equal to a second central apnoea threshold during the ventilation cycle;

means for determining whether the ventilation cycle is a normal cycle; and means for increasing the pressure of the air flow to the patient above the maintenance pressure when the ventilation cycle is determined to be a normal cycle, the presence of an apnoea is detected and the sum of the occurrence of central apnoeas is less than or equal to the second central apnoea threshold.

14. The apparatus of claim 13, wherein the means for determining whether a ventilation cycle of air flow to the patient is a normal cycle includes means for calculating a mean amplitude of the flow air to the patient of during the ventilation cycle, and means for designating the ventilation cycle as not a normal cycle when the mean amplitude is greater than a first hyperventilation factor.

15. The apparatus of claim 13, further comprising:
means for measuring the pressure of the air flow to the patient;
means for setting a high pressure time counter to zero when the pressure of the air flow to the patient is less than a high pressure threshold;
means for incrementing the high pressure time counter when the pressure of the air flow to the patient is not less than the high pressure threshold; and
means for reducing the pressure of the air flow to the patient to a safety pressure value when the value of the high pressure time counter is greater than a maximum high pressure time threshold.

16. The apparatus of claim 13, further comprising means for measuring a leakage of air flow to the patient during the ventilation cycle, and means for maintaining the pressure of the air flow to the patient when the measured air leakage is greater than a leakage level threshold.

17. The apparatus of claim 16, further comprising means for setting the leakage level threshold to substantially equal to an additive leakage value summed with a leakage coefficient multiplied by the measured air flow to the patient.

18. The apparatus of claim 13, further comprising means for analyzing the detected oscillations within an acoustic frequency range so as to identify acoustic vibrations, and means for increasing the pressure of the air flow to the patient when acoustic vibrations are identified.

* * * * *